US008160315B2

(12) United States Patent
Hayashi et al.

(10) Patent No.: US 8,160,315 B2
(45) Date of Patent: Apr. 17, 2012

(54) ULTRASONIC IMAGING APPARATUS AND PROJECTION IMAGE GENERATING METHOD (75) Inventors: Tetsuya Hayashi, Kashiwa (JP); Osamu Arai, Tsukuba (JP)

(73) Assignee: Hitachi Medical Corporation, Tokyo (JP)

( * ) Notice: Subject to any disclaimer, the term of this patent is extended or adjusted under 35 U.S.C. 154(b) by 982 days.

(21) Appl. No.: 11/575,166

(22) PCT Filed: Sep. 12, 2005

(86) PCT No.: PCT/JP2005/016745
§ 371 (c)(1),
(2), (4) Date: Jun. 9, 2008

(87) PCT Pub. No.: WO2006/030731
PCT Pub. Date: Mar. 23, 2006

(65) Prior Publication Data
US 2008/0260227 A1 Oct. 23, 2008

(30) Foreign Application Priority Data
Sep. 13, 2004 (JP) .................. 2004-265158

(51) Int. Cl.
*A61B 8/00* (2006.01)
*A61B 8/121* (2006.01)

(52) U.S. Cl. ........ 382/128; 382/130; 382/131; 600/441; 600/447; 600/453

(58) Field of Classification Search .......... 382/128–133; 600/407–464
See application file for complete search history.

(56) References Cited

U.S. PATENT DOCUMENTS

| 5,720,291 | A | * | 2/1998 | Schwartz | 600/456 |
| 5,857,973 | A | | 1/1999 | Ma et al. | |
| 5,860,924 | A | * | 1/1999 | Quistgaard | 600/441 |
| 6,280,387 | B1 | * | 8/2001 | Deforge et al. | 600/454 |
| 6,416,476 | B1 | * | 7/2002 | Ogasawara et al. | 600/443 |
| 2006/0241458 | A1 | * | 10/2006 | Hayashi et al. | 600/453 |

FOREIGN PATENT DOCUMENTS

| JP | 07-213522 | * | 8/1995 |
| JP | 09-262236 | | 10/1997 |
| JP | 2001-017428 | | 1/2001 |
| JP | 2005-143733 | | 6/2005 |

* cited by examiner

*Primary Examiner* — Melissa Koval
*Assistant Examiner* — Emily Chan
(74) *Attorney, Agent, or Firm* — Antonelli, Terry, Stout & Kraus, LLP.

(57) ABSTRACT

A three-dimensional ultrasonic image with which the positional relationship between tissues can be surely grasped is generated. Accordingly, an ultrasonic imaging apparatus and a projection image generating method according to the present invention acquire first three-dimensional image data and second three-dimensional image data, generate a first projection image on the basis of at least a part of the first three-dimensional image data and the second three-dimensional image data, and generate a second projection image on the basis of at least a part of the second three-dimensional image data and the first three-dimensional imaged data.

35 Claims, 8 Drawing Sheets

$Cout = Cin(1-\alpha(x)) + c(x) \cdot \alpha(x)$

ULTRASONIC IMAGING APPARATUS AND PROJECTION IMAGE GENERATING METHOD

TECHNICAL FIELD

The present invention relates to an ultrasonic imaging apparatus and a projection image generating method, and particularly to a technique suitable for generating a three-dimensional ultrasonic image.

BACKGROUND ART

An ultrasonic imaging apparatus transmits/receives ultrasonic waves to/from an object being examined through an ultrasonic probe, and reconstructs and displays an ultrasonic image (for example, grayscale tomographic image, a color blood stream image) of the object being examined on the basis of a reflection echo signal output from the ultrasonic probe. A noninvasive and real-time diagnosis of an image pickup site can be performed on the basis of such an ultrasonic image.

In the ultrasonic imaging apparatus as described above, three-dimensional tomographic image data (hereinafter referred to as tomogram volume data) and three-dimensional Doppler image data (hereinafter referred to as Doppler image volume data) are obtained on the basis of the reflection echo signal output from the ultrasonic probe, and a tissue projection image generated from the obtained tomogram volume data and a Doppler projection image generated from the Doppler image volume data are combined with each other and displayed. On the basis of this composite image, for example, the positional relationship between a blood vessel and tissues around the blood vessel is grasped, and the state of a nutrient vessel of a cancer tissue is recognized from the positional relationship, whereby it is judged whether the cancer tissue is protopathic or metastatic (for example, see Patent Document 1).

Patent Document 1: see U.S. Pat. No. 6,280,387

However, when a tissue projection image and a Doppler projection image are combined and displayed as in the case of the Patent Document 1, an image at the point-of-view side of a diagnosing person is preferentially displayed, and thus a part of the Doppler projection image may hide in the tissue projection image. Accordingly, in order to surely grasp the stereoscopic positional relationship between the blood vessel and the tissues around the blood vessel (for example, the penetration state of the blood vessel through the tissues), it is necessary to carry out an operation of rotating the display angle of the composite image or remove unnecessary image data from the composite image, and thus there is a problem that this device is inconvenient.

Furthermore, when the tissue projection image and the Doppler projection image are displayed in superposition with each other while varying the composition rate between the tissue projection image and the Doppler projection image, the brightness of the respective images is equally changed in connection with the change of the composition rate, and thus it is difficult to grasp, from the displayed composite image, the stereoscopic positional relationship between the blood vessel and the tissue around the blood vessel, for example, the overlap condition of the respective images when viewed from the projection direction, depth feel in the projection direction in the overlap area, etc.

DISCLOSURE OF THE INVENTION

A problem of the present invention is to generate a three-dimensional ultrasonic image with which the positional relationship of tissues can be surely grasped.

In order to solve the above problem, an ultrasonic imaging apparatus according to the present invention comprises: an ultrasonic probe (10) for transmitting/receiving ultrasonic waves to/from an object being examined; transmission means (12) for supplying a driving signal to the ultrasonic probe (10); reception means (14) for receiving a reflection echo signal output from the ultrasonic probe (10); signal processing means (18, 20) for subjecting the reflection echo signal output from the reception means to signal processing; volume data generating means (19, 21) for generating first volume data and second volume data on the basis of the signal-processed reflection echo signal; storage means (26) for storing the two volume data; and projection image generating means (28) for generating a first projection image on the basis of rendering processing of the first volume data and generating a second projection image on the basis of rendering processing of the second volume data, wherein the projection image generating means generates the first projection image on the basis of at least parts of the first volume data and second volume data, and generates the second projection image on the basis of at least parts of the second volume data and the first volume data.

In order to solve the problem, according to the present invention, a method of generating a projection image comprises a first accumulating step of accumulating plural first two-dimensional image data; a first three-dimensional imaging step of generating first volume data from the plural first two-dimensional image data; a second accumulating step of accumulating plural second two-dimensional image data; a second three-dimensional imaging step of generating second volume data from the plural second two-dimensional image data; a first projection step of generating a first projection image by subjecting the first volume data to rendering processing; and a second projection step of generating a second projection image by subjecting the second volume data to rendering processing, wherein the first projection step generates the first projection image on the basis of at least parts of the first volume data and second volume data, and the second projection step generates the second projection image on the basis of at least parts of the second volume data and first volume data.

According to this invention, the first projection image is generated by adding the first three-dimensional image data with the information of the second three-dimensional image data, and thus the information on the overlap with the second three-dimensional image data is reflected to brightness every pixel. Accordingly, by referring to the shading (grayscale) of the first projection image, the overlap condition with the second three-dimensional image data can be grasped, and a stereoscopic and effective diagnosis can be easily performed.

Likewise, the second projection image is generated by adding the second three-dimensional image data with the information of the first three-dimensional image data, and thus the information on the overlap with the first three-dimensional image data is reflected to brightness every pixel. Accordingly, by referring to the shading of the second projection image, the overlap condition with the first three-dimensional image data can be grasped, and a stereoscopic and effective diagnosis can be easily performed.

According to the present invention, there can be generated a three-dimensional ultrasonic image with which the positional relationship between tissues (for example, a blood vessel and the surrounding area of the vessel) can be surely grasped.

BEST MODES FOR CARRYING OUT THE INVENTION

Figure 1:
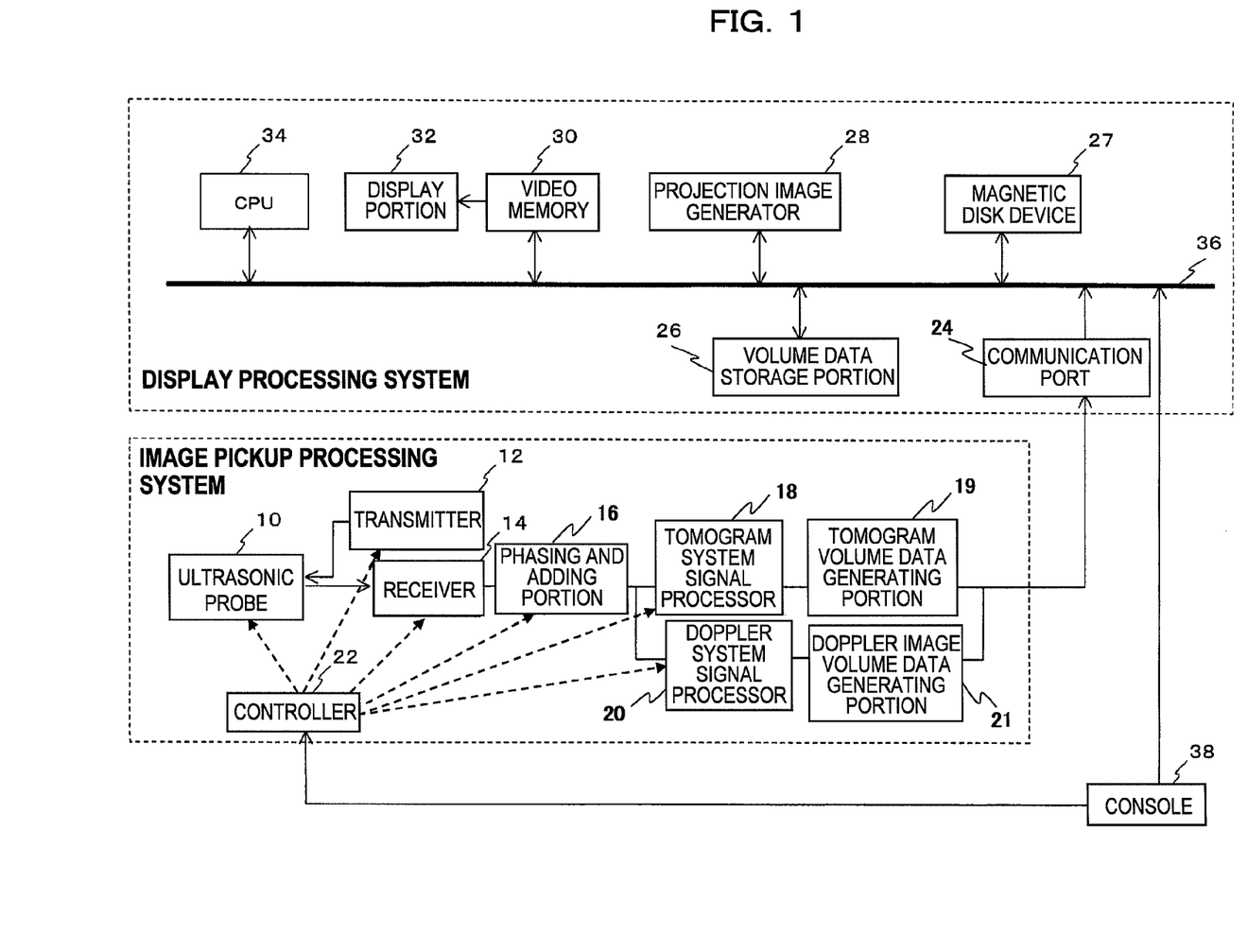
[FIG. 1] is a diagram showing the construction of an ultrasonic wave imaging apparatus according to an embodiment to which the present invention is applied.

An embodiment of an ultrasonic imaging apparatus and a projection image generating method to which the present invention is applied will be described with reference to FIGS. 1 to 8. FIG. 1 is a diagram showing the construction of an ultrasonic imaging apparatus of this embodiment.

As shown in FIG. 1, the ultrasonic imaging apparatus is roughly divided into an image pickup processing system of obtaining a three-dimensional ultrasonic image volume data of an object being examined and a display processing system of displaying the obtained three-dimensional ultrasonic image volume data.

The imaging apparatus is equipped with an ultrasonic probe 10 including plural vibrators that are arranged two-dimensionally and transmit/receive ultrasonic waves to/from an object being examined, a transmitter 12 for supplying a driving signal to the ultrasonic probe 10, a receiver 14 for receiving a reflection echo signal output from the ultrasonic probe 10, and a phasing and adding portion 16 for phasing and adding the reflection echo signal output from the receiver 14. A tomogram system signal processor 18 and a tomogram volume data generating portion 19 are provided as means of acquiring the tomogram volume data on the basis of the reflection echo signal output from the phasing and adding portion 16. Furthermore, a Doppler image type signal processor 20 and a Doppler image volume data generating portion 21 are provided as means of obtaining Doppler image volume data on the basis of the reflection echo signal output from the phasing and adding portion 16. Furthermore, there is also provided a controller 22 for outputting control instructions (dotted lines having arrows of FIG. 1) to the ultrasonic probe 10, the transmitter 12, the receiver 14, the phasing and adding portion 16, the tomogram system signal processor 18, and the Doppler image type signal processor 20.

The display processing system is equipped with a communication port 24 for taking in tomogram volume data and Doppler image volume data output from the image pickup processing system, a volume data storage portion 26 for storing each volume data output from the communication port 24, a projection image generator 28 for generating a projection image on the basis of the volume data read out from the volume data storage portion 26, and a display portion 32 for displaying the projection image generated by the projection image generator 28 on a display screen of a monitor through a video memory 30. Furthermore, there is also provided a central processing unit (hereinafter referred to as CPU 34) for outputting control instructions to the communication port 24, the volume data storage portion 26, the projection image generator 28, the video memory 30 and the display portion 32.

The communication port 24, the volume data storage portion 26, the projection image generator 28, the video memory 30, the display portion 32 and CPU 34 are mutually connected to one another through a common bus 36. A magnetic disk device 27 may be provided as an auxiliary storage device of the volume data storage portion 26. However, the auxiliary storage device is not limited to the magnetic disk device 27, and other storage devices such as DVD-R, etc. may be provided.

A console 38 is connected to the image pickup processing system and the image processing system. The console 38 has input devices such as a keyboard, a mouse, etc., and it outputs an instruction input through an input device to the controller 22 of the image pickup processing system and also to CPU 34 of the image processing system through the common bus. For convenience of description, the controller 22 and CPU 34 are separated from each other in the following example, however, an integral type control device having the respective control functions may be used.

Figure 2:
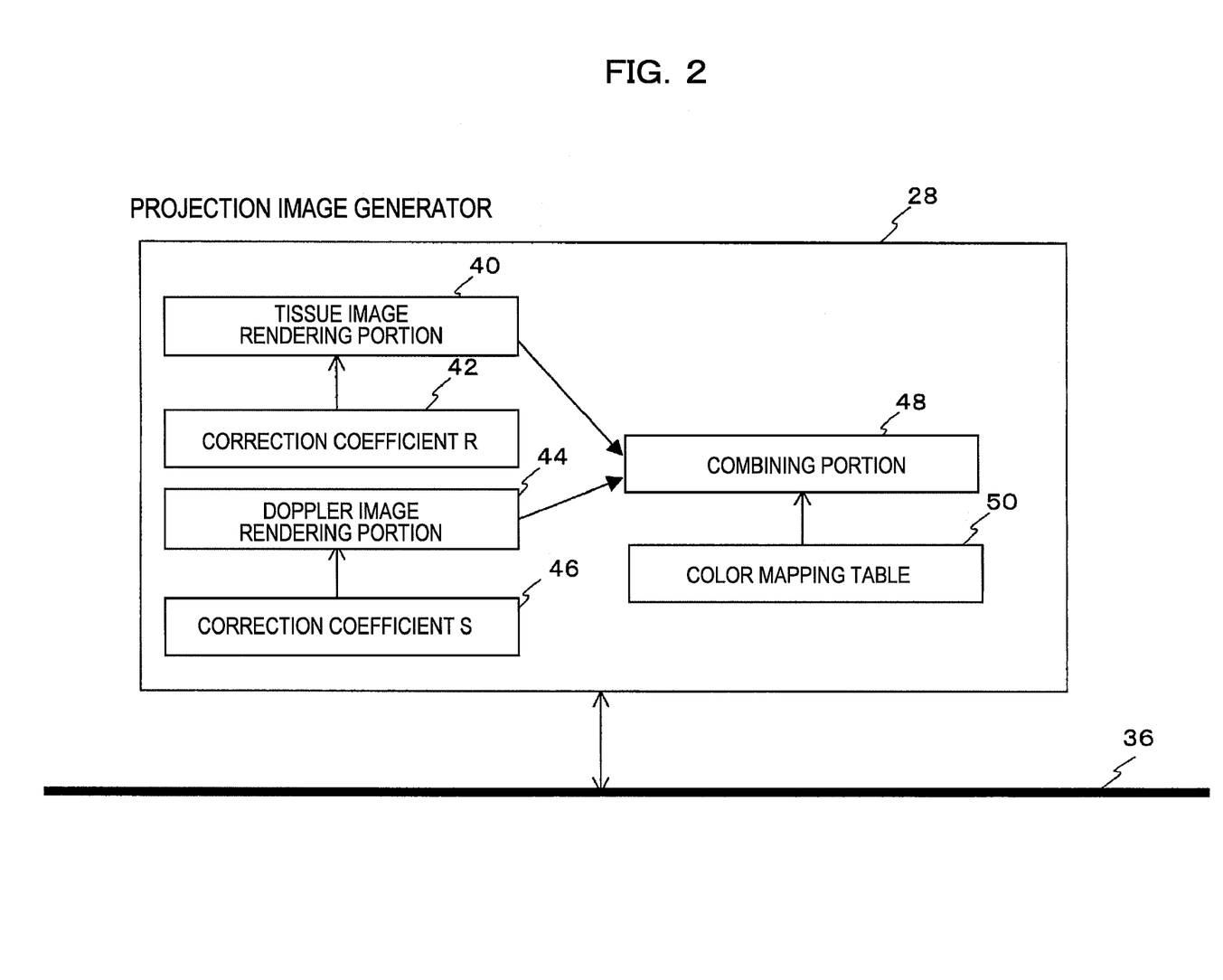
[FIG. 2] is a diagram showing the construction of a projection image generator 28 of FIG. 1.

FIG. 2 is a diagram showing the construction of the projection image generator 28 of FIG. 1. As shown in FIG. 2, the projection image generator 28 is equipped with a tissue image rendering portion 40 for correcting the information belonging to each voxel of the tomogram volume data read out from the volume data storage portion 26 on the basis of the information belonging to each voxel of the Doppler image volume data, and generating a grayscale (for example, monochromatic) tissue projection image from the corrected tomogram volume data. Furthermore, the projection image generator 28 is also provided with a memory 42 for storing a correction coefficient (blend coefficient) R (or R1, R2 described later) given to the tissue image rendering portion 40.

Furthermore, the projection image generator 28 is also provided with a Doppler image rendering portion 44 for correcting information belonging to each voxel of the Doppler image volume data read out from the volume data storage portion 26 on the basis of the information belonging to each voxel of the tomogram volume data, and generating a colored Doppler projection image from the corrected Doppler image volume data. Furthermore, the projection image generator 28 has a memory 46 for storing a correction coefficient (blend coefficient) S (or S1, S2 described later) given to the Doppler image rendering portion 44. The correction coefficient R, S (or R1, R2, S1, S2 described later) is variable set in the range from "0" to "1" on the basis of an instruction from the console 38. It may be set to a fixed value.

Furthermore, the projection image generator 28 is provided with a combining portion 48 for superposing the tissue projection image generated by the tissue image rendering portion 40 and the Doppler projection image generated by the Doppler image rendering portion 44 to generate a composite image, and displaying the generated composite image on the display portion 32. There is provided a memory 50 for storing a combining color mapping table for giving color data to the composite image.

The operation of the thus-constructed ultrasonic imaging apparatus will be described. First, the ultrasonic probe 10 is brought into contact with the body surface of the object being examined. A driving signal for picking up an image of a tissue is supplied from the transmitter 12 to the ultrasonic probe 10. The supplied driving signal is input to a predetermined vibrator group selected in response to an instruction from the controller 22. Accordingly, ultrasonic wave is emitted to the object being examined from each vibrator to which the driving signal is input. A reflection echo signal occurring from the object being examined is received by each vibrator, and then output from the ultrasonic probe 10. The reflection echo signal output from the ultrasonic probe 10 is subjected to amplification processing, analog digital conversion processing, etc. by the receiver 14. The reflection echo signal output from the receiver 14 is subjected to processing such as detection, etc. by the tomogram system signal processor 18, thereby acquiring monochromatic tomogram data based on the signal intensity of the reflection echo signal.

The image pickup of the tissue as described above is repetitively carried out on plural scan planes set at predetermined slice intervals, thereby obtaining plural tomographic image data corresponding to the respective scan planes. Each obtained tomographic image data are input to the tomogram volume data generating portion 19. The input plural tomographic image data are constructed as tomogram volume data by giving position data (for example, the coordinate data of each scan plane) to each voxel by the tomogram volume data generating portion 19. The constructed tomogram volume data are stored in the volume data storage portion 26 through the communication port 24.

Furthermore, the driving signal for picking up an image of a blood stream is supplied from the transmitter 12 to the ultrasonic probe 10, whereby ultrasonic waves are emitted from the ultrasonic probe 10 to the object being examined. A reflection echo signal occurring from the object being examined is received by each vibrator, and then output from the ultrasonic probe 10. The reflection echo signal output from the ultrasonic probe 10 is input to the Doppler image type signal processor 20 through the receiver 14 and the phasing and adding portion 16. The Doppler shift (for example, the frequency variation or phase variation of the reflection echo signal) is calculated on the basis of the input reflection echo signal by the Doppler image type signal processor 20. Then, colored Doppler image data such as the blood stream speed, the reflection intensity, dispersion, etc. are obtained from the calculated Doppler shift.

The blood current image pickup as described above is repetitively carried out on plural scan planes set at predetermined slice intervals, thereby acquiring plural Doppler image data corresponding to the respective scan planes. Each obtained Doppler image data are input to the Doppler image volume data generating portion 21. The plural input Doppler image data are constructed as Doppler image volume data by giving the position data (for example, the coordinate data of the respective scan planes) to each voxel by the Doppler volume data generating portion 21. The constructed tomogram volume data are stored in the volume data storage portion 26 through the communication port 24.

The tomogram volume data and the Doppler image volume data stored in the volume data storage portion 26 are read out in response to an instruction of CPU 34, and then input to the projection image generator 28. On the basis of the input tomogram volume data, the monochromatic tissue projection image is generated by the projection image generator 28. The color Doppler projection image is generated on the basis of the read-out Doppler image volume data by the projection image generator 28. The generated tissue projection image and the Doppler projection image are superposed on each other so that the position data of each pixel is identical to each other, whereby a composite image is displayed on the display portion 32. When the tomogram volume data and the Doppler image volume data are stored in the magnetic disk device 27, each volume data may be read out from the magnetic disk device 27, and then input to the projection image generator 28.

Figure 3:
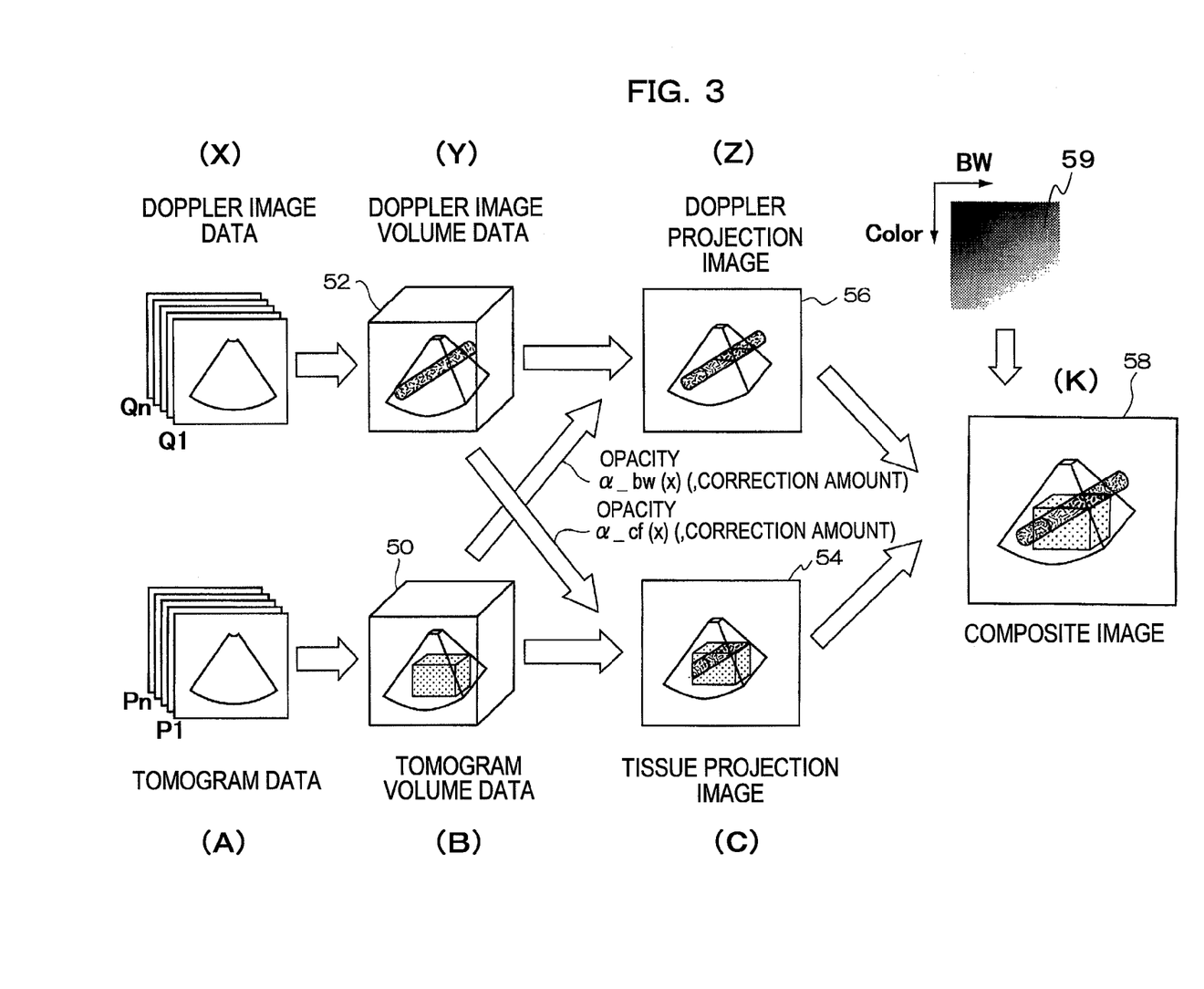
[FIG. 3] is a diagram showing the operation of generating a composite image.

FIG. 3 is a diagram showing the operation of generating respective projection images and the composite image thereof. As shown in FIG. 3, tomogram volume data 50 is constructed on the basis of plural tomogram data P1 to Pn (FIG. 3(A)) (FIG. 3(B)). Furthermore, Doppler image volume data 52 is constructed on the basis of plural Doppler image data Q1 to Qn (FIG. 3(X)) (FIG. 3(Y)).

The tomogram volume data 50 is subjected to volume rendering processing on the basis of a set observing direction (line of vision) through the console 38 by the tissue image rendering portion 40, whereby a tissue projection image 54 is generated (FIG. 3(C)). In the volume rendering processing, the tissue image rendering portion 40 corrects the information belonging to each voxel of the tomogram volume data 50 on the basis of the information belonging to each voxel of the Doppler image volume data 52, and generates the tissue projection image 54 on the basis of the tomogram volume data 50 and the corrected information.

For example, when opacity and attenuance are determined as the information belonging to each voxel, the tissue image rendering portion 40 corrects the attenuance of the voxel determined from the opacity belonging to each voxel of the tomogram volume data 50 on the basis of the opacity belonging to the voxel of the Doppler image volume data which corresponds to the above voxel, and a correction coefficient R which is variably set by the console 38, and then generates the tissue projection image 54 on the basis of the tomogram volume data 50, the opacity and the corrected attenuance.

The Doppler image volume data 52 is subjected to volume rendering processing on the basis of the observing direction set through the console 38 by the Doppler image rendering portion 44, there by generating a Doppler projection image 56 (FIG. 3(Z)). In the volume rendering processing, the Doppler image rendering portion 44 corrects the information belonging to each voxel of the Doppler image volume data 52 on the basis of the information belonging to each voxel of the tomogram volume data 50, and generates the Doppler projection image 56 on the basis of the Doppler image volume data 52 and the corrected information.

For example, when opacity and attenuance are determined as the information belonging to each voxel, the tissue image rendering portion 40 corrects the attenuance of the voxel determined from the opacity belonging to each voxel of the Doppler image volume data 52 on the basis of the opacity belonging to the voxel of the tomogram volume data 50 corresponding to the above voxel, and a correction coefficient S which is variably set by the console 38, and generates the Doppler projection image 56 on the basis of the Doppler image volume data 52, the opacity and the corrected attenuance.

The tissue projection image 54 and the Doppler projection image 56 are superposed on each other so that the coordinate data of each pixel is identical therebetween, thereby generating a composite image 58 (FIG. 3(K)).

When two projection images 54 and 56 are combined with each other, it is carried out by using a color mapping table 59. The color mapping table 59 represents the brightness value of the tissue projection image 54 set on the abscissa axis, the brightness value of the Doppler projection image 56 set on the ordinate axis and the brightness value of the corresponding composite image 58 by using a two-dimensional map. For example, when the brightness value of the tissue projection image 54 is represented by "a" and the brightness value of the Doppler projection image 56 is represented by "b", the value at a point (a,b) on the color mapping table 59 corresponds to the value (color and brightness) of the composite image 58.

Figure 8:
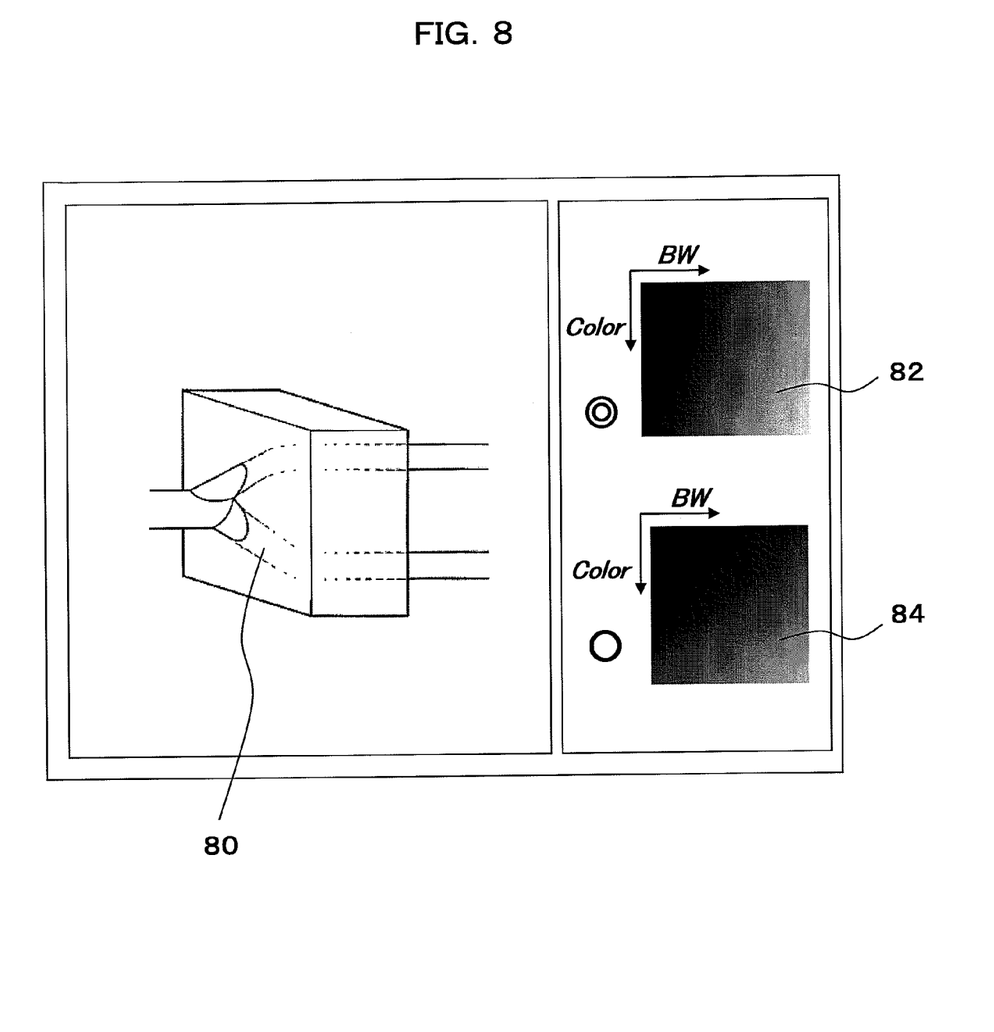
[FIG. 8] is a diagram showing an example of displaying plural different color mapping tables and generating a composite image on the basis of a selected map.

By preparing plural color mapping tables and generating a composite image on the basis of a selected color mapping table, it is possible to adjust the composition rate between the tissue projection image and the Doppler projection image, that is, which one of the images should be emphasized. This example is shown in FIG. 8. FIG. 8 shows an example in which two different color mapping tables 82 and 84 and a composite image 80 formed on the basis of a selected color mapping table 82 are displayed at the right side and the left side respectively in juxtaposition with each other on the display portion 32. The selection of the color mapping table is carried out by an input from the console 39. In the example of FIG. 8, the selected state of the table is indicated in the neighborhood of each table by using a mark indicating a selected state of the table ◉ or non-selected state of the table ○.

The color mapping table 82 is a table for emphasizing a monochromatic tissue projection image, and it has a small amount of color component as a whole. On the other hand, a color mapping table 84 is a table for emphasizing a color Doppler projection image, and it has a large amount of color component. By selecting any one of the color mapping tables, a composite image is formed on the basis of the color mapping table concerned. Furthermore, even after the composite image is formed, by changing the selected color mapping table, a composite image can be reconstructed on the basis of a newly selected color mapping table. FIG. 8 shows an example in which two different color mapping tables are displayed, however, the number of the color mapping tables displayed may be equal to three or more.

After the composite image is formed as described above, at least one of the tissue projection image 54, the Doppler projection image 56 and the generated composite image 58 is displayed on the display screen of the display portion 32. It is preferable that the composite image is preferentially displayed.

In the foregoing description, the tissue projection image and the Doppler projection image are generated, and these two projection images are combined with each other to generate a composite image. However, only any one projection image of the tissue projection image and the Doppler projection image may be generated. Preferably, only the projection image generated from the volume data having a larger information amount may be generated. That is, the projection image is generated from the volume data having a larger information amount while adding the volume data having a smaller information amount. In the above case, the tomogram volume data generally has a larger information amount than the Doppler image volume data, and thus only the tissue projection image to which the overlap condition with the current stream image is reflected can be selectively generated. It is needless to say that only the Doppler projection image may be selectively generated as occasion demands. When only any one projection image is generated, it is unnecessary to determine attenuance every voxel of the other volume data. It is also unnecessary to generate the composite image described above.

Alternatively, one projection image may be generated as in the case of the above embodiment, the other projection image may be generated on the basis of only the volume data thereof as in the case of the prior art, and these two projection images may be combined with each other. For example, the tissue projection image may be generated as in the case of the above embodiment, the Doppler projection image may be generated from only the Doppler image volume data as in the case of the prior art, and these two projection images may be combined with each other to generate a composite image. Conversely, the tissue projection image may be generated from only the tomogram volume data as in the case of the prior art, the Doppler projection image may be generated as in the case of the above embodiment, and these two projection images may be combined with each other to generate a composite image.

Figure 4:
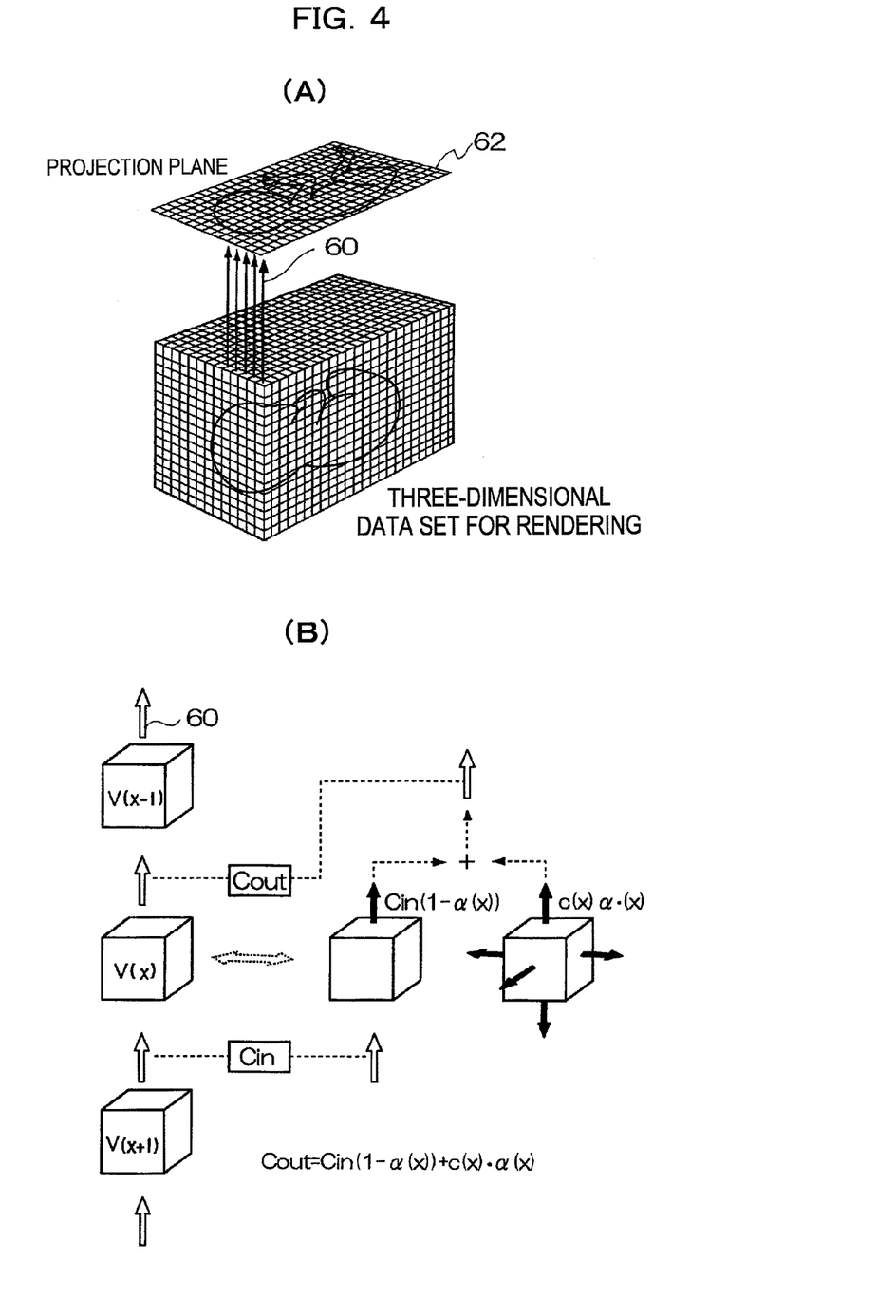
[FIG. 4] is a diagram showing normal volume rendering processing.

Next, the volume rendering processing of the tissue image rendering portion 40 and the Doppler image rendering portion 44 will be described in detail. Therefore, general volume rendering processing will be first described with reference to FIG. 4. FIG. 4 shows the general volume rendering processing when a pre-born child is a image pickup target, and it is cited from a document (Kazunori Baba, yuko Io: Department of Obstetrics and Gynecology Three-dimensional Ultrasonic Wave, Medical View, Tokyo, 2000).

FIG. 4(A) is a diagram showing the concept of the volume rendering. As shown in FIG. 4(A), the volume rendering is a method of executing a predetermined calculation on the brightness value of voxels on lines 60 penetrating through the three-dimensional volume data to determine the brightness of each point on a projection plane 62. Here, the lines 60 are parallel to the observing direction (the visual line direction) set through the console 38.

FIG. 4(B) is a diagram showing the concept of the calculation method of determining the brightness of each point on the projection plane 62. As shown in FIG. 4(B), when the value V(x) of a voxel at the position x on one line 60 is noted, the output light amount Cout of the voxel V(x) is represented according to the equation 1 when the incident light amount to the voxel V(x) is represented by Cin, the opacity of the voxel V(x) is represented by α(x) and the self light emission amount of the voxel V(x) is represented by C(x). As is apparent from the equation 1, the output light amount Cout of the voxel V(x) is determined attenuating the incident light amount Cin to the voxel V(x) in accordance with the attenuance (1−α(x)) and also adding the light emission amount C(x)×α(x) of the voxel V(x) itself.

$$Cout = Cin \times (1-(x)) + C(x) \times \alpha(x) \qquad \text{(equation 1)}$$

Here, the self light emission amount C(x) is a function of the voxel V(x), and for example, it can be set to a logarithm function of the voxel V(x) (C(x)=a×logV(x)+b; a, b are constants). That is, the self light emission amount α(x) is a value produced by subjecting the voxel value V(x) to predetermined conversion, or it may be the voxel value V(x) itself (in short, C(x)=V(x)).

Figure 6:
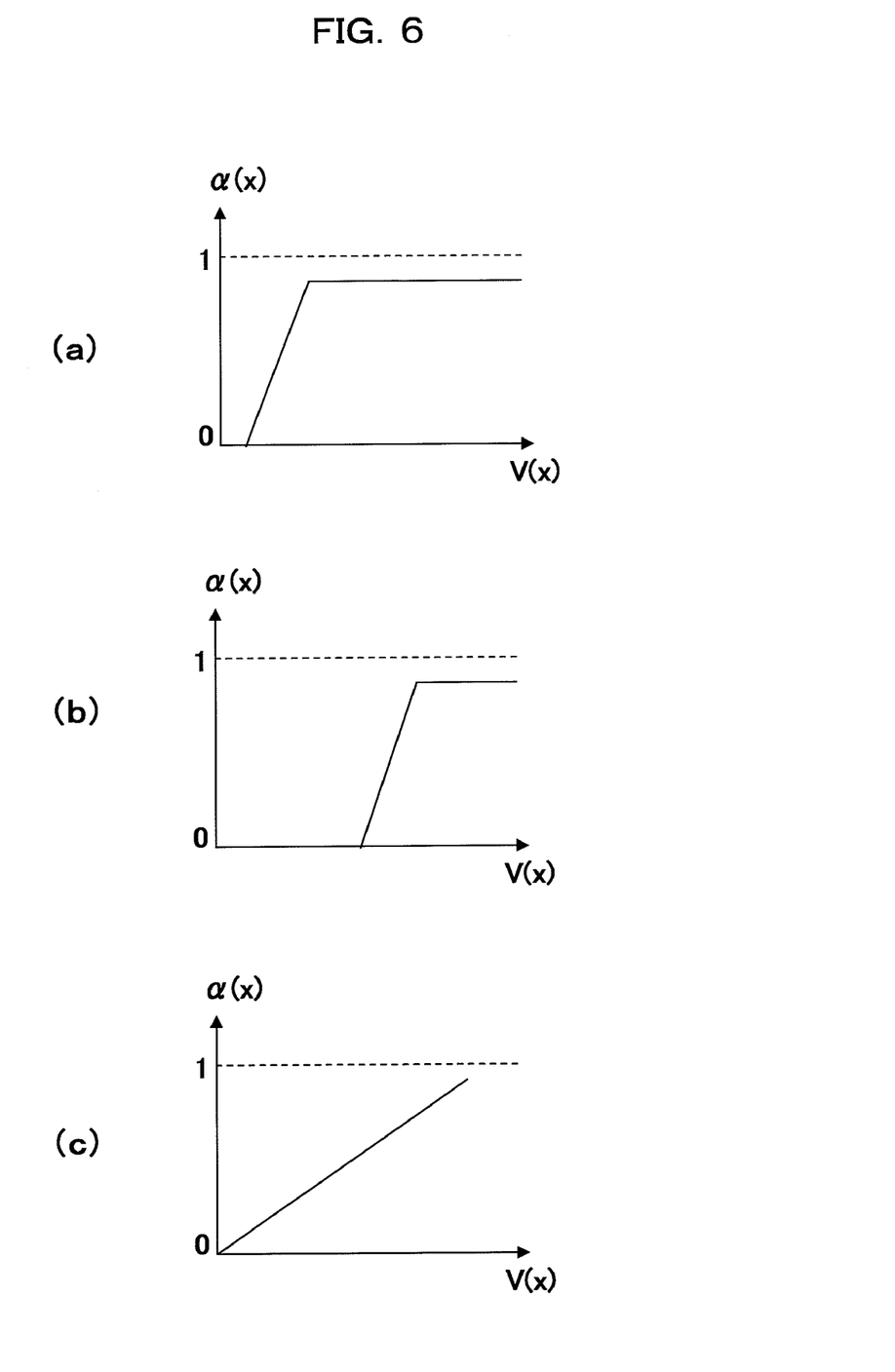
[FIG. 6] is a diagram showing the relationship of introducing opacity from voxel values.

Furthermore, the opacity α(x) is a value in the range from "0" to "1", and it means that the voxel V(x) is more transparent as the value is nearer to "0" and it is more opaque as the value is nearer to "1". The opacity α(x) can be settled by the voxel value V(x). This example is shown in FIG. 6. In the example of FIG. 6(a), the opacity α(x) is set to a large value from a low value of the voxel value V(x), whereby the shape of the surface of an object being examined at the light incident side is greatly reflected to the projection image. Conversely, in the example of FIG. 6(b), the opacity α(x) is set to a large value from a higher value of the voxel value V(x), whereby the shape of a site having large brightness (that is, a site having a large voxel value V(x)) in the object being examined is greatly reflected to the projection image. In the example of FIG. 6(c), the opacity α(x) is set in proportion to the voxel value V(x), whereby the overall volume is substantially equally reflected to the image projection.

Next, the volume rendering processing of the tissue image rendering portion 40 and the Doppler image rendering portion 44 according to the present invention will be described.

The tissue image rendering portion 40 corrects the attenuance of the voxel Vbw(x) of the tomogram volume data 50 on the basis of the opacity belonging to the voxel Vcf(x) of the Doppler image volume data 52 and a variably-set correction coefficient R, and the tissue projection image 54 is generated on the basis of the tomogram volume date 50, the opacity and the corrected attenuance. For example, when the self light emission amount of the voxel Vbw(x) of the tomogram volume data 50 is represented by Cbw(x), the opacity is represented by $\alpha\_bw(x)$, and the opacity of the voxel Vcf(x) of the Doppler image volume data 52 is represented by $\alpha\_cf(x)$, the output light amount Cout of the voxel Vbw(x) of the tomogram volume data 50 is represented according to the equation 2. In short, the original attenuance $(1-\alpha\_bw(x))$ of the voxel Vbw(x) is corrected to a new attenuance $(1-\alpha\_bw(x)+\alpha\_cf(x)\times R)$.

$$\text{Cout}=\text{Cin}\times(1-\alpha\_bw(x)+\alpha\_cf(x)\times R)+Cbw(x)\times\alpha\_bw(x) \quad \text{(equation 2)}$$

Likewise, the Doppler image rendering portion 44 corrects the attenuance of the voxel Vcf(x) of the Doppler image volume data 52 on the basis of the opacity belonging to the voxel Vbw(x) of the tomogram volume data 50 and the variably-set correction coefficient S, and generates the Doppler projection image 56 on the basis of the Doppler image volume data 52, the opacity and the corrected attenuance. For example, when the self light emission amount of the voxel Vcf(x) the Doppler image volume data 52 is represented by Ccf(x), the opacity is represented by $\alpha\_cf(x)$, and the opacity of the voxel Vbw(x) of the tomogram volume data 54 is represented by $\alpha\_bw(x)$, the output light amount Cout of the voxel Vcf(x) of the Doppler image volume data 52 is represented according to the equation 3. In short, the original attenuance $(1-\alpha\_cf(x))$ of the voxel Vcf(x) is corrected to a new attenuance $(1-\alpha\_cf(x))+\alpha\_bw(x)\times S)$.

$$\text{Cout}=\text{Cin}\times(1-\alpha\_cf(x)+\alpha\_bw(x)\times S)+Ccf(x)\times\alpha\_cf(x) \quad \text{(equation 3)}$$

Furthermore, as shown in FIG. 3, the output light amount Cout of the voxel Vbw(x) of the tomogram volume data 50 may be calculated by adding a correction amount based on the light emission amount $(=Ccf(x)\times\alpha\_cf(x))$ of the voxel Vcf(x) of the Doppler image volume data 52. That is, the output light amount Cout may be calculated according to the equation 4.

$$\text{Cout}=\text{Cin}\times(1-\alpha\_bw(x)+\alpha\_cf(x)\times R1)+Cbw(x)\times\alpha\_bw(x)+Ccf(x)\times\alpha\_cf(x)\times R2 \quad \text{(equation 4)}$$

Here, the last term $(Ccf(x)\times\alpha\_cf(x)\times R2)$ is the correction amount, and R1 and R2 are correction coefficients which are variably set in the range from "0" to "1". If R1=R and R2=0, this equation is identical to the equation 2. Or these values may be set so that R1=0 and R2≠0.

Likewise, as shown in FIG. 3, the output light amount Cout of the voxel Vcf(x) of the Doppler image volume data 52 can be calculated by adding a correction amount based on the light emission amount $(=Cbw(x)\times\alpha\_bw(x))$ of the voxel Vbw(x) of the tomogram volume data 50. That is, the output light amount Cout can be calculated according to the equation 5.

$$\text{Cout}=\text{Cin}\times(1-\alpha\_cf(x)+\alpha\_bw(x)\times S1)+Ccf(x)\times\alpha\_cf(x)+Cbw(x)\times\alpha\_bw(x)\times S2 \quad \text{(equation 5)}$$

Here, the last term $(Cbw(x)\times\alpha\_bw(x)\times S2)$ is the correction amount, and S1 and S2 are correction coefficients which are variably set in the range from "0" to "1". If S1=S and S2=0, this equation is identical to the equation 3. Alternatively, these values may be set so that S1=0 and S2≠0.

The brightness of each point on the projection plane is determined on the basis of the output light amount Cout of the tomogram volume data 50 which is calculated according to the calculation method as described above, thereby generating the tissue projection image 54. Likewise, the Doppler projection image 56 is generated on the basis of the output light amount Cout of the Doppler image volume data 52.

According to this embodiment, the tissue projection image 54 is generated by adding the information belonging to each voxel of the Doppler image volume data 52 of the tomogram volume data 50, and thus the overlap condition with the Doppler image is reflected to the brightness every pixel. Accordingly, by referring to the grayscale of the tissue projection image 54, the overlap condition of the blood vessel in the tissue can be easily grasped, and a stereoscopic and effective diagnosis can be performed. Particularly, the projection image is obtained by adding the correction amount as shown in the equation 4, whereby the overlap condition of the blood vessel in the tissue can be more clearly and easily grasped than the projection image obtained according to the equation 2 adding no correction amount.

For example, the attenuance of the voxel V(x) with which the Doppler image is overlapped, out of the respective voxels (x) of the tomogram volume data 50, is corrected. Accordingly, when the tissue projection image 54 is generated on the basis of the tomogram volume data 50 and the corrected attenuance, in the generated tissue projection image 54, the overlap condition with the blood stream image is reflected as a shadow every pixel (FIG. 3(C)). As a result, by referring to the grayscale of the shadow of the tissue projection image 54, the overlap condition of the blood vessel in the tissue can be easily grasped.

The Doppler projection image 56 is generated by adding the information belonging to each voxel V(x) of the tomogram volume data 50 to the Doppler image volume data 52, so that the overlap condition with the tomographic image is reflected to the brightness every pixel. Accordingly, by referring to the Doppler projection image 56, the overlap condition of the tissue in the blood vessel can be easily grasped. Particularly, the projection image is determined by adding the correction amount according to the equation 5, whereby the overlap condition of the tissue in the blood vessel can be more clearly and easily grasped than the projection image using the equation 3 in which no correction amount is added.

For example, the attenuance of the voxel V(x) with which the tomographic image is overlapped, out of the respective voxels V(x) of the Doppler image volume data 52 is corrected.

Accordingly, when the Doppler projection image 56 is generated on the basis of the Doppler image volume data 52 and the corrected attenuance, in the generated Doppler projection image 56, the overlap condition with the tomographic image is reflected as a shadow every pixel. As a result, by referring to the grayscale of the shadow of the Doppler projection image 56, the overlap condition of the tissue in the blood vessel can be simply grasped.

Furthermore, in both the tissue projection image 54 and the Doppler projection image 56, the overlap condition is reflected as a shadow. Therefore, by combining the tissue projection image 54 and the Doppler projection image 56, a composite image 58 in which the stereoscopic positional relationship between the blood vessel and the tissue surrounding the blood vessel is accurately represented is displayed on the display portion 32. Accordingly, by referring to the displayed composite image 58, the stereoscopic positional relationship between the blood vessel and the tissue surrounding the blood vessel can be readily grasped.

Furthermore, the correction coefficients R, S (or R1, R2, S1, S2) can be made variable through the console 38 as occasion demands, and thus the grayscale of the shadow appearing in the tissue projection image 54 or the Doppler projection image 56 can be adjusted. Accordingly, the composite image can be displayed in accordance with, for example, the tissue characteristic of an image pickup site, whereby the visibility of the composite image indicating the stereoscopic positional relationship between the blood vessel and the tissue around the blood vessel can be enhanced.

Figure 5:
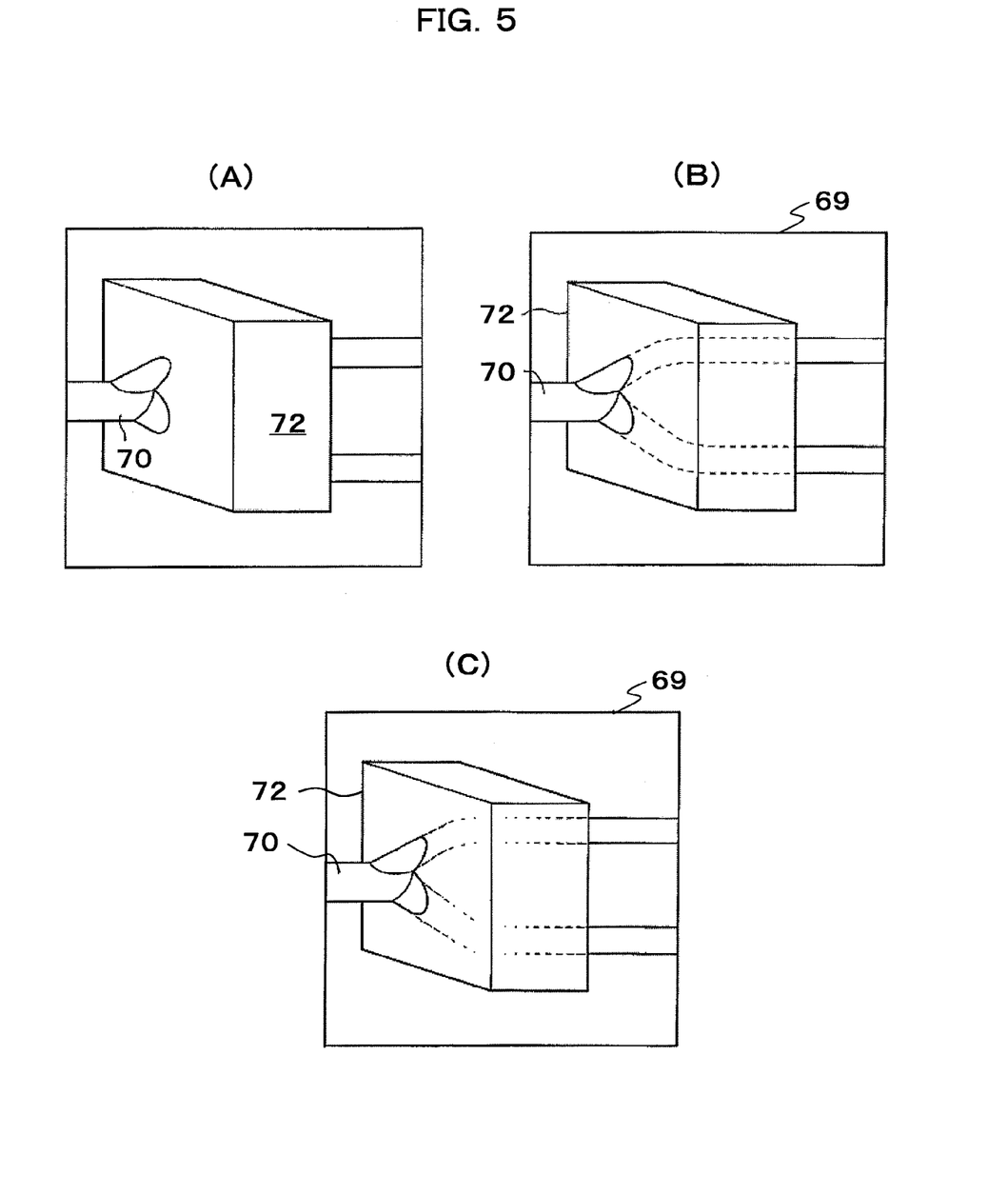
[FIG. 5] is a display example of a composite image 69 constructed by phantom.

FIG. 5 shows a display example of a composite image 69 which is constructed by using phantom. FIG. 5(A) shows a display example of the composite image 69 constructed by setting both the correction coefficients R, S (or R1, R2, S1, S2) to "0", and FIG. 5(B) shows a display example of the composite image 69 constructed by setting the correction coefficient R (or R1, R2) to "1" and setting S (or S1, S2) to "0.1". It is understood that a blood vessel invading to the deep site of the tissue is displayed because the contribution rate of the tomogram volume data to the Doppler projection image is low (that is, the correction coefficient S is small) although the blood vessel invades into the tissue. Furthermore, FIG. 5(C) shows a display example of the composite image 69 constructed by setting the correction coefficients R, S (or R1, R2, S1, S2) to "1", and it is surely understood that the blood vessel gradually disappears as the blood vessel invades into the tissue more deeply (that is, the aspect of the overlap condition between the blood vessel and the tissue in the projection direction is surely understood). The generation of the composite image by setting both the correction coefficients R, S to "0" is similar to the prior art, however, the composite image generated by setting both the correction coefficients R, S to values other than "0" is the composite image according to the present invention.

According to the composite image 69 of FIG. 5(A), the image at the view point side of a diagnosing person is preferentially displayed, and thus a part of the Doppler projection image 70 is hidden in the tissue projection image 72. Accordingly, it is difficult to surely grasp the stereoscopic positional relationship between the blood vessel and the tissue around the blood vessel (for example, the penetration state of the object associated with the Doppler projection image 70 through the object associated with the tissue projection image 72).

The tissue projection image 72 and the Doppler projection image 70 in which the correction coefficients R, S (or R1, R2, S1, S2) are set to "0" are identical to the projection images of the prior art which are independently generated with no addition of the volume data information. In the prior art, the composite image 69 is generated at a predetermined composite rate from the tissue projection image 72 and the Doppler projection image 70 generated as described above. By making the composite rate variable, any one of the tissue projection image 72 and the Doppler projection image 70 can be displayed with being emphasized. However, the brightness of each pixel of the tissue projection image 72 or the Doppler projection image 70 is equally changed in connection with the variation of the composite rate, and thus it is difficult to grasp the stereoscopic positional relationship between the blood vessel and the tissue around the blood vessel from the composite image displayed as described above.

On the other hand, according to the composite image 69 of FIG. 5(B) and FIG. 5(C) of the present invention, the Doppler projection image 70 and the tissue projection image 72 are translucently displayed, and thus the stereoscopic positional relationship between the Doppler projection image 70 and the tissue projection image 72 can be surely and readily visualized.

The tissue projection image 72 and the Doppler projection image 70 generated by setting the correction coefficients R, S (or R1, R2, S1, S2) to values other than "0" are generated with being added with the volume data information, and thus the mutual stereoscopic positional relationship is clearly reflected even in the composite image 69. Accordingly, the stereoscopic positional relationship between the blood vessel and the tissue around the blood vessel can be easily grasped, and thus information effective to diagnosis of, for example, a cancer can be easily obtained.

Figure 7:
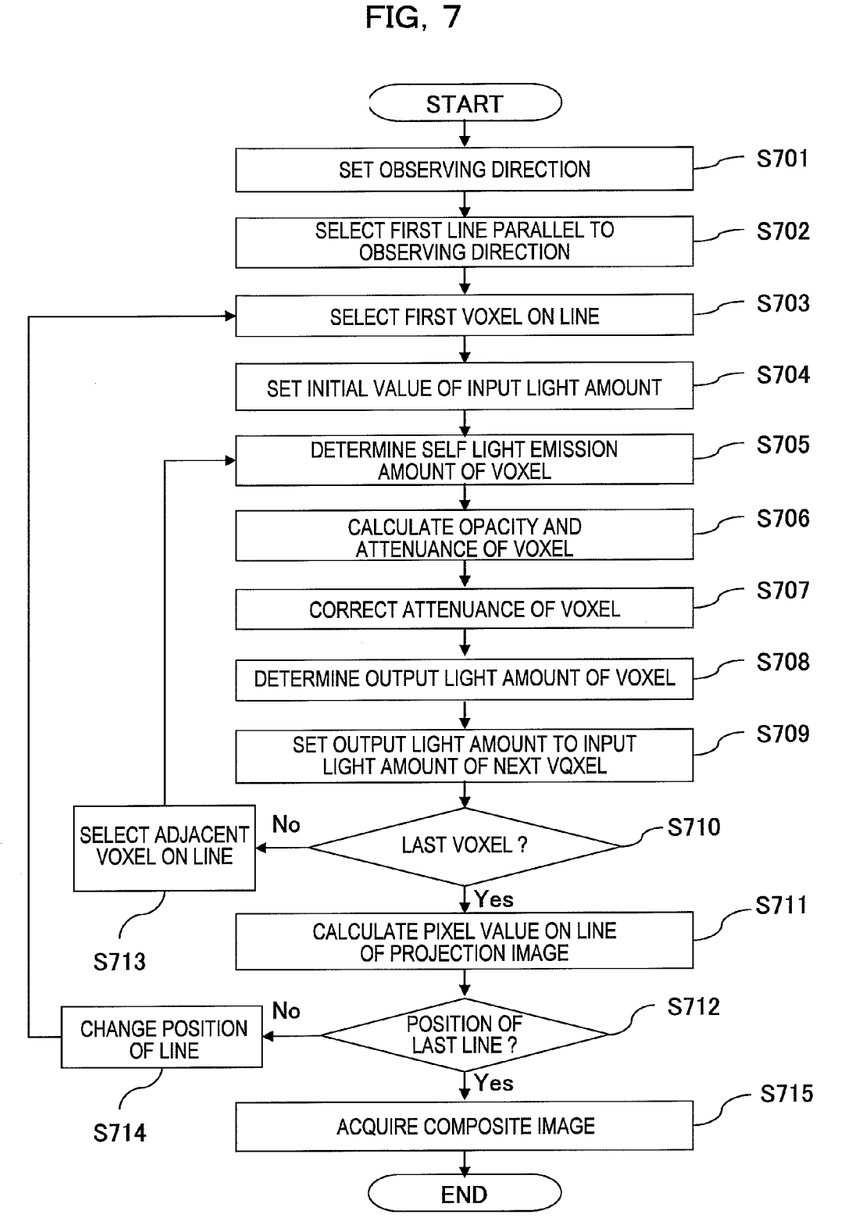
[FIG. 7] is a flowchart showing the processing flow of determining a projection image and a composite image.

Next, FIG. 7 shows the flow of the respective steps from the generation of each projection image to the generation of the composite images from these projection images after the tomogram volume data and the Doppler image volume data are obtained. Each processing step in this flowchart will be individually described. The detailed description of each processing step has been made as described above, and thus it is omitted. Only the rough outline thereof will be described.

In step S701, an observing direction (visual line direction) for generating a projection image is set. A plane perpendicular to the observing direction is a projection plane.

In step S702, a first line parallel to the observing direction set in step S701 is selected.

In step S703, first voxels on the line selected in step S702 are selected in two volume data.

In step S704, initial values of the input light amount Cin are set in the two volume data. For example, they can be set to "0"

In step S705, the self light emission amount Cbw(x) of the voxel concerned is determined by using the voxel value Vbw(x) of the tomogram volume data. Furthermore, the self light emission amount Ccf(x) of the voxel is determined by using the voxel value Vcf(x) of the Doppler image volume data.

In step S706, the opaque ($\alpha\_bw(x)$) and the attenuance ($1-\alpha\_bw(x)$) of this voxel are calculated by using the voxel value Vbw(x). Furthermore, the opaque ($\alpha\_cf(x)$) and the attenuance ($1-\alpha\_cf(x)$) of the voxel are calculated by using the voxel value Vcf(x).

In step S707, the attenuance of the voxel Vbw(x) and the attenuance of the voxel Vcf(x) are corrected. For example, when the equation 2 is used, the attenuance ($1-\alpha\_bw(x)$) is corrected by using the opaque ($\alpha\_cf(x)$) and the correction coefficient R, and the corrected attenuance is represented by ($1-\alpha\_bw(x)+\alpha\_cf(x)\times R$). Furthermore, when the equation 3 is used, the attenuance ($1-\alpha\_cf(x)$) is corrected by using the opaque ($\alpha\_bw(x)$) and the correction coefficient S, and the corrected attenuance is represented by ($1-\alpha\_cf(x)+\alpha\_bw(x)\times S$). When the equations 4 and 5 are used, the correction amount to be added when the output light amount Cout is calculated is determined.

In step S708, the output light amount Cout of the voxel Vbw(x) is calculated by using the equation 2 or the equation 4. Furthermore, the output light amount Cout of the voxel Vcf(x) is calculated by using the equation 3 or the equation 5.

In step S709, the output light amount Cout calculated in step S708 is set to the input light amount Cin of the next voxel.

In step S710, it is checked whether the voxel is the last voxel on the line. If it is the last voxel, the processing shifts to step S711, and if not so, the processing shifts to step S713.

In step S711, the output light amount Cout of the last voxel Vbw(x) is set to the value of a pixel of the tissue projection image on the line. Furthermore, the output light amount Cout of the last voxel Vcf(x) is set to the value of a pixel of the Doppler projection image on the line.

In step S712, it is checked whether the line is the last position or not. If it is the last line, all the pixel values of the tissue projection image and the Doppler projection images are determined, and thus the processing shifts to step S715. If not so, the processing shifts to step S714.

In step S713, adjacent voxels on the line are selected in both the tomogram volume data and the Doppler image volume data, and then the processing shifts to step S705.

In step S714, the positions of the parallel lines in the observing direction are changed in the tomogram volume data and the Doppler image volume data, and then the processing shifts to step S703.

In step S715, the tissue projection image and the Doppler projection image are combined with each other on the basis of the color mapping table, thereby acquiring the composite image.

The present invention has been described on the basis of the embodiment, however, the present invention is not limited to the above embodiment. For example, an ultrasonic probe having a position sensor may be used in place of the ultrasonic probe 10 having the plural two-dimensionally arranged vibrators. In short, any style may be adopted insofar as the position data of the scan plane to be supplied to each voxel of the tomogram volume data or the Doppler image volume data can be obtained.

Furthermore, with respect to the driving signal for picking up the image of the tissue and the driving signal for picking up the image of the blood stream, it can be time-divisionally supplied from the transmitter 12 to the ultrasonic probe 10, whereby the tomogram volume data 50 and the Doppler image volume data 52 can be substantially simultaneously crated. However, the present invention is not limited to the time-divisional supply style, and any style may be adopted insofar as the tomogram volume data and the Doppler image volume data can be obtained. With respect to the driving signal for picking up the image of the tissue, the signal corresponding to a single pulse wave is preferably used to enhance the image resolution of the tissue tomographic image. Furthermore, with respect to the driving signal for picking up the image of the blood stream, a signal having plural (for example, eight) linked single pulse waves is preferably used to facilitate the detection of Doppler shift.

Furthermore, a region of interest (ROI) may be set through the console 38 so as to surround a display target (for example, cancerous tissue or pre-born child). Accordingly, a surrounding unnecessary portion can be removed, and thus the processing speed of the tissue image rendering portion 40 or the Doppler image rendering portion 44 can be enhanced.

The examples of the tomogram volume data and the Doppler image volume data have been described. However, the present invention is not limited to these images, and the projection image generating method of the present invention is applicable to two different volume data.

The invention claimed is:

1. A projection image generating method of generating a projection image including information on at least a part of a first three-dimensional image and information on at least a part of a second three-dimensional image, comprising:
    a first accumulating step of accumulating plural first two-dimensional image data;
    a first three-dimensional imaging step of generating first three-dimensional image data from the plural first two-dimensional image data;
    a second accumulating step of accumulating plural second two-dimensional image data;
    a second three-dimensional imaging step of generating second three-dimensional image data from the plural second two-dimensional image data;
    a first projecting step of subjecting the first three-dimensional image data to rendering processing to generate a first projection image; and
    a second projecting step of subjecting the second three-dimensional image data to rendering processing to generate a second projection image, wherein the first projecting step generates the first projection image on the basis of the first three-dimensional image data and at least a part of the second three-dimensional image data, and the second projecting step generates the second projection image on the basis of the second three-dimensional image data and at least a part of the first three-dimensional image data,
    wherein the first projecting step corrects information of at least a partial area of the first projection image on the basis of the second three-dimensional image data, and the second projecting step corrects information of at least a partial area of the second projection image on the basis of the first three-dimensional image data.

2. The projection image generating method according to claim 1, wherein the first projecting step corrects information of at least a partial area of the first projection image on the basis of the second three-dimensional image data at the same position as the first three-dimensional image data, and the second projecting step corrects information of at least a partial area of the second projection image on the basis of the first three-dimensional image data at the same position as the second three-dimensional image data.

3. The projection image generating method according to claim 2, wherein on the basis of the second three-dimensional image data at an overlap portion with the first three-dimensional image data, the first projecting step corrects information of the area of the first projection image that corresponds to the overlap portion, and on the basis of the first three-dimensional image data at an overlap portion with the second three-dimensional image data, the second projecting step corrects information of the area of the second projection image that corresponds to the overlap portion.

4. The projection image generating method according to claim 1, wherein the first projecting step corrects brightness of at least a partial area of the first projection image on the basis of the second three-dimensional image data, and the second projecting step corrects brightness of at least a partial area of the second projection image on the basis of the first three-dimensional image data.

5. The projection image generating method according to claim 4, wherein the first projecting step corrects the brightness of at least a partial area of the first projection image on the basis of the second three-dimensional image data so that the brightness reflects the overlap condition in the projection direction of the two three-dimensional image data, and the second projecting step corrects the brightness of at least a partial area of the second projection image on the basis of the first three-dimensional image data so that the brightness reflects the overlap condition in the projection direction of the two three-dimensional image data.

6. The projection image generating method according to claim 1, wherein only any one of the first projecting step and the second projecting step is selected and executed.

7. The projection image generating method according to claim 6, wherein the step of generating the projection image based on one of the first three-dimensional image data and the second three-dimensional image data is selected, the one image data having a larger information amount.

8. The projection image generating method according to claim 1, wherein the first projecting step comprises:
    a first calculating step of obtaining first information from the first three-dimensional image data;
    a first correcting step of correcting the first information corresponding to at least a partial area of the first projection image on the basis of the second three-dimensional image data; and a first projection image generating step of generating the first projection image on the basis of the first three-dimensional image data and the corrected first information.

9. The projection image generating method according to claim 8, wherein the first calculating step calculates opacity by using the value of each voxel of the first three-dimensional image data every voxel and calculates attenuance from the opacity, the second projecting step has a second calculating step of calculating opacity by using the value of each voxel of the second three-dimensional image data every voxel, the first correcting step corrects the attenuance of each voxel of the first three-dimensional image data by using the opacity of each voxel of the second three-dimensional image data, and the first projection image generating step generates the first projection image on the basis of the first three-dimensional image data, the opacity and the corrected attenuance.

10. The projection image generating method according to claim 9, wherein the second calculating step calculates the attenuance of each voxel of the second three-dimensional image data from the opacity of each voxel, and the second projecting step comprises a second correcting step of correcting the attenuance of each voxel of the second three-dimensional image data that corresponds to at least a partial area of the second projection image by using opacity of each voxel of the first three-dimensional image data, and a second projection image generating step of generating the second projection image on the basis of the second three-dimensional image data, and the opacity and the corrected attenuance thereof.

11. The projection image generating method according to claim 10, wherein the first correcting step corrects the attenuance of each voxel of the first three-dimensional image data by using a multiplication value of the opacity of each voxel of the second three-dimensional image data and a first correction coefficient, and the second correcting step corrects the attenuance of each voxel of the second three-dimensional image data by using a multiplication value of the opacity of each voxel of the first three-dimensional image data and a second correction coefficient.

12. The projection image generating method according to claim 10, wherein each of the first projection image generating step and the second projection image generating step comprises:
(a) a step of setting an observing direction;
(b) a step of selecting a first line parallel to the observing direction;
(c) a step of selecting a first voxel on the line in three-dimensional image data;
(d) a step of setting an initial value of an input light amount to the voxel;
(e) a step of determining a self light emission amount of the voxel by using the voxel value;
(f) a step of calculating the opacity and attenuance of the voxel by using the value of the voxel;
(g) a step of correcting the attenuance of the voxel by using the opacity of the corresponding voxel of the other three-dimensional image data corresponding to the voxel;
(h) a step of determining an output light amount of the voxel from the sum of a multiplication value of the input light amount and the corrected attenuance and a multiplication value of the self light emission amount and the opacity;
(i) a step of selecting an adjacent voxel to the above voxel on the line in the three-dimensional tissue image data;
(j) a step of setting the output light amount of the voxel to the input light amount of the adjacent voxel;
(k) a step of repeating (e) to (j);
(l) a step of setting the output light amount as a pixel value of a projection image on the line;
(m) a step of changing the position on the line; and
(n) a step of repeating (d) to (m).

13. The projection image generating method according to claim 1, wherein the second projection step comprises:
a second calculating step of acquiring second information from the second three-dimensional image data;
a second correcting step of correcting the second information corresponding to at least a partial area of the second projection image on the basis of the first three-dimensional image data; and
a second projection image generating step of generating the second projection image on the basis of the second three-dimensional image data and the corrected second information.

14. The projection image generating method according to claim 1, wherein the first accumulating step accumulates tomographic image data as the first two-dimensional image data, the first three-dimensional imaging step generates three-dimensional tomographic image data as the first three-dimensional image data, the second accumulating step accumulates Doppler image data as the second two-dimensional image data, the second three-dimensional imaging step generates three-dimensional Doppler image data as the second three-dimensional image data, the first projection image generating step generates a tissue projection image as the first projection image, and the second projection image generating step generates a Doppler projection image as the second projection image.

15. The projection image generating method according to claim 1, further comprising a combining step of combining the first projection image and the second projection image with each other after the projection image generating step, thereby generating a composite image.

16. The projection image generating method according to claim 15, wherein the combining step determines pixel values of the composite image on the basis of a color mapping table in which the pixel value of the first projection image is set to one axis, and the pixel value of the second projection image is set to the other axis.

17. The projection image generating method according to claim 15, further comprising a step of displaying at least one of the first projection image, the second projection image and the composite image.

18. An ultrasonic imaging apparatus having an ultrasonic probe for transmitting/receiving ultrasonic waves to/from an object being examined, transmission means configured to supply a driving signal to the ultrasonic probe, reception means configured to receive a reflection echo signal output from the ultrasonic probe, signal processing means configured to process the reflection echo signal output from the reception means, three-dimensional image data generating means configured to generate first three-dimensional image data and second three-dimensional image data on the basis of the signal-processed reflection echo signal, storage means configured to store the two three-dimensional image data, and projection image generating means configured to generate a first projection image by executing rendering processing on the first three-dimensional image data and generating a second projection image by executing rendering processing on the second three-dimensional image data, wherein that the projection image generating means generates the first projection image on the basis of at least a part of the first three dimensional image data and the second three dimensional image data, and generates the second projection image on the basis of at least a part of the second three-dimensional image data and the first three-dimensional image data, and wherein the projection image generating means generates only at least a partial area of one of the projection images on the basis of the two three-dimensional image data.

19. The ultrasonic imaging apparatus according to claim 18, wherein the projection image generating means generates a composite image by combining the first projection image and the second projection image.

20. An ultrasonic imaging apparatus, comprising:
an ultrasonic probe for transmitting/receiving ultrasonic waves to/from an object being examined;
a transmitter for supplying a drive signal to the ultrasonic probe;
a receiver for receiving a reflection echo signal output from the ultrasonic probe;
a phasing and adding portion for accumulating plural first two-dimensional image data and plural second two-dimensional image data;
a volume data generator for generating a first three-dimensional image data and a second three-dimensional image data from the plural first and second two-dimensional image data, respectively;
a data storage portion for storing the first three-dimensional image data and the second three-dimensional image data; and
a projection image generator for generating a first rendered projection image based on the first three-dimensional image data and at least part of the second three-dimensional image data, and generating a second rendered projection image based on the second three-dimensional image data and at least part of the first three-dimensional image data,
wherein the projection image generator corrects information of at least a partial area of the first projection image based on the second three-dimensional image data, and
wherein the projection image generator corrects information of at least a partial area of the second projection image based on the first three-dimensional image data.

21. The ultrasonic imaging apparatus according to claim 20, wherein the projection image generator corrects information of at least a partial area of the first projection image based on the second three-dimensional image data at the same position as the first three-dimensional image data, and corrects information of at least a partial area of the second projection image based on the first three-dimensional image data at the same position as the second three-dimensional image data.

22. The ultrasonic imaging apparatus according to claim 21, wherein the projection image generator corrects information of the partial area of the first projection image that corresponds to an overlap portion when the second three-dimensional image data is at the overlap portion with the first three-dimensional image data, and
wherein the projection image generator corrects information of the partial area of the second projection image that corresponds to an overlap portion when the first three-dimensional image data is at the overlap portion with the second three-dimensional image data.

23. The ultrasonic imaging apparatus according to claim 20, wherein the projection image generator corrects brightness of at least a partial area of the first projection image based on the second three-dimensional image data, and corrects brightness of at least a partial area of the second projection image based on the first three-dimensional image data.

24. The ultrasonic imaging apparatus according to claim 23, wherein the projection image generator corrects the brightness of at least a partial area of the first projection image based on the second three-dimensional image data so that the brightness reflects an overlap condition in a projection direction of the first and second three-dimensional image data, and
wherein the projection image generator corrects the brightness of at least a partial area of the second projection image based on the first three-dimensional image data so that the brightness reflects an overlap condition in the projection direction of the first and second three-dimensional image data.

25. The ultrasonic imaging apparatus according to claim 20, wherein the projection image generator only generates one of the first rendered projection image and the second rendered projection image.

26. The ultrasonic imaging apparatus according to claim 25, wherein the projection image generator selects a rendered projection image to generate based on a corresponding three-dimensional image data containing a larger information amount.

27. The ultrasonic imaging apparatus according to claim 20, wherein the projection image generator is configured to generate the first projecting step by:
acquiring first information from the first three-dimensional image data;
correcting the first information corresponding to at least a partial area of the first projection image based on the second three-dimensional image data; and
generating step of generating the first projection image on the basis of the first three-dimensional image data and the corrected first information.

28. The ultrasonic imaging apparatus according to claim 27, wherein projection image generator is configured to:
calculate a first opacity by using the value of each voxel of the first three-dimensional image data every voxel and a first attenuance from the first opacity,
calculate a second opacity by using the value of each voxel of the second three-dimensional image data every voxel,
correct a first attenuance of each voxel of the first three-dimensional image data by using the second opacity, and
generates the first projection image based on the first three-dimensional image data, the first opacity, and the corrected first attenuance.

29. The ultrasonic imaging apparatus according to claim 28, wherein the projection image generator is configured to:
calculate the attenuance of each voxel of the second three-dimensional image data from the second opacity of each voxel,
corrects a second attenuance of each voxel of the second three-dimensional image data that corresponds to at least a partial area of the second projection image by using the first opacity of each voxel of the first three-dimensional image data,
generates the second projection image base on the second three-dimensional image data, the second opacity, and the corrected second attenuance.

30. The ultrasonic imaging apparatus according to claim 29, wherein:
the first attenuance is corrected by using a multiplication value of the second opacity and a first correction coefficient, and
the second attenuance is corrected by using a multiplication value of the first opacity and a second correction coefficient.

31. The ultrasonic imaging apparatus according to claim 20, wherein the projection image generator is configured to generate the second projection step by:
acquiring second information from the second three-dimensional image data;

correcting the second information corresponding to at least a partial area of the second projection image on the basis of the first three-dimensional image data; and generating the second projection image on the basis of the second three-dimensional image data and the corrected second information.

32. The ultrasonic imaging apparatus according to claim 20, wherein:

the phasing and adding portion accumulates tomographic image data as the first two-dimensional image data and accumulates Doppler image data as the second two-dimensional image data, the volume data generator generates three-dimensional tomographic image data as the first three-dimensional image data and generates three-dimensional Doppler image data as the second three-dimensional image data, and the projection image generator generates a tissue projection image as the first rendered projection image and generates a Doppler projection image as the second rendered projection image.

33. The ultrasonic imaging apparatus according to claim 20, wherein the projection image generator combines the first projection image and the second projection image to generate a composite image.

34. The ultrasonic imaging apparatus according to claim 33, wherein the projection image generator determines pixel values of the composite image based on a color mapping table in which the pixel value of the first projection image is set to one axis, and the pixel value of the second projection image is set to another axis.

35. The ultrasonic imaging apparatus according to claim 33, further comprising a display unit for displaying at least one of the first projection image, the second projection image, and the composite image.

* * * * *